United States Patent
Pingali et al.

(10) Patent No.: US 10,991,053 B2
(45) Date of Patent: Apr. 27, 2021

(54) LONG-TERM HEALTHCARE COST PREDICTIONS USING FUTURE TRAJECTORIES AND MACHINE LEARNING

(71) Applicant: DZee Solutions, Inc., Centennial, CO (US)

(72) Inventors: Ashwin K. Pingali, Parker, CO (US); Srikar Appana, Denver, CO (US)

(73) Assignee: DZee Solutions, Inc., Centennial, CO (US)

( * ) Notice: Subject to any disclaimer, the term of this patent is extended or adjusted under 35 U.S.C. 154(b) by 774 days.

(21) Appl. No.: 15/202,431

(22) Filed: Jul. 5, 2016

(65) Prior Publication Data

US 2017/0004279 A1 Jan. 5, 2017

Related U.S. Application Data

(60) Provisional application No. 62/188,253, filed on Jul. 2, 2015, provisional application No. 62/199,338, filed on Jul. 31, 2015.

(51) Int. Cl.
| | |
|---|---|
| G06Q 40/00 | (2012.01) |
| G16H 50/50 | (2018.01) |
| G06F 19/00 | (2018.01) |
| G06Q 10/10 | (2012.01) |

(52) U.S. Cl.
CPC .............. *G06Q 40/12* (2013.12); *G06F 19/00* (2013.01); *G16H 50/50* (2018.01); *G06Q 10/10* (2013.01)

(58) Field of Classification Search
CPC ........ G06Q 40/12; G06Q 50/22; G16H 50/50; G06F 19/00
USPC ....................................................... 705/2–4
See application file for complete search history.

(56) References Cited

U.S. PATENT DOCUMENTS

| | | | | |
|---|---|---|---|---|
| 6,687,685 | B1 * | 2/2004 | Sadeghi ............... | G06F 19/3418 600/300 |
| 7,024,399 | B2 * | 4/2006 | Sumner, II .......... | G06F 19/3481 706/45 |
| 7,689,521 | B2 * | 3/2010 | Nodelman ........... | G06Q 10/109 706/21 |

(Continued)

OTHER PUBLICATIONS

Bouayad, Lina. "Analytics and Healthcare Costs (A Three Essay Dissertation)." (2015).*

*Primary Examiner* — Mark Holcomb
(74) *Attorney, Agent, or Firm* — Holzer Patel Drennan

(57) ABSTRACT

The disclosed technology includes a system for modeling progression of lifetime healthcare expenses, including healthcare events resulting in an out-of-pocket expenditure per a given healthcare plan, wherein each healthcare event is associated with a group of healthcare events. Each group of healthcare events is associated with different sets of certainty with different groups of individuals. A central computing device communicates with healthcare event data generation sources to obtain the healthcare event data. A static database module stores the healthcare event data in hierarchical layered graphs. A dynamic database module dynamically generates data that depicts different future expenditures over a life span based on the healthcare event data in the static database module. A computer modeling module generates the most likely set of future expenditures using the different future expenditures data in the dynamic database module.

17 Claims, 11 Drawing Sheets

(56) References Cited

U.S. PATENT DOCUMENTS

| | | | | |
|---|---|---|---|---|
| 7,813,870 | B2* | 10/2010 | Downs | G08G 1/0104 340/995.13 |
| 10,496,678 | B1* | 12/2019 | Tang | G06F 16/282 |
| 2004/0039710 | A1* | 2/2004 | McMillan | G06Q 10/04 705/400 |
| 2005/0240544 | A1* | 10/2005 | Kil | G06F 19/00 706/45 |
| 2006/0085230 | A1* | 4/2006 | Brill | G06F 19/328 705/4 |
| 2011/0166883 | A1* | 7/2011 | Palmer | G06Q 10/10 705/3 |
| 2012/0116850 | A1* | 5/2012 | Abe | G06Q 10/067 705/7.38 |
| 2013/0159023 | A1* | 6/2013 | Srinivas | G06F 19/00 705/4 |
| 2013/0191153 | A1* | 7/2013 | Lee | G16H 50/20 705/3 |
| 2014/0149128 | A1* | 5/2014 | Getchius | G06Q 50/22 705/2 |
| 2014/0343965 | A1* | 11/2014 | Miyoshi | G16H 50/20 705/3 |
| 2016/0117322 | A1* | 4/2016 | Ramaswamy | G06F 21/6218 707/756 |
| 2016/0203279 | A1* | 7/2016 | Srinivas | G06Q 40/08 705/2 |
| 2016/0292304 | A1* | 10/2016 | Kartha | G06N 5/027 |

\* cited by examiner

LONG-TERM HEALTHCARE COST PREDICTIONS USING FUTURE TRAJECTORIES AND MACHINE LEARNING

CROSS REFERENCE TO RELATED APPLICATIONS

The present application claims priority to pending U.S. Provisional Patent Application Ser. No. 62/188,253, entitled "Machine-Learning Based Classification and Permutation Engine," filed on Jul. 2, 2015, and pending U.S. Provisional Patent Application Ser. No. 62/199,338, entitled "Machine Learning-Based Classification and Permutation Engine" filed Jul. 31, 2015. Both of these applications are specifically incorporated by reference for all that they disclose or teach.

BACKGROUND

Healthcare costs are increasingly shifting towards individuals before and after retirement as the cost of healthcare continues to outpace inflation and GDP growth. As a result, this shift has resulted in individuals filing for bankruptcy due to their inability to meet the out-of-pocket costs related to their healthcare events.

Healthcare cost forecasting mechanisms for individuals and family units can assist financial planning for these healthcare costs. Calculators provide models and indicators for healthcare expenses based on determinate factors, such as Medicare premiums. However, models and indicators are static in nature, resulting in relatively inaccurate projections when used to calculate costs over long periods of time. Inaccuracies in financial projections are unreliable and make it difficult for individuals to efficiently plan for their healthcare costs.

SUMMARY

The disclosed technology includes a system for modeling progression of lifetime healthcare expenses, including healthcare events resulting in an out-of-pocket expenditure per a given healthcare plan, wherein each healthcare event is associated with a group of healthcare events. Each group of healthcare events is associated with different sets of certainty with different groups of individuals. A central computing device communicates with healthcare event data generation sources to obtain healthcare event data, including out-of-pocket expenditures, plan profiles, and event and subevent groups that categorize individuals based on personal factors. A static database module stores the healthcare event data in hierarchical layered graphs. A dynamic database module dynamically generates data that depicts different future expenditures over a life span based on the healthcare event data in the static database module. A computer modeling module generates the most likely set of future expenditures using the different future expenditures data in the dynamic database module.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. These and various other features and advantages will be apparent from a reading of the following Detailed Descriptions.

BRIEF DESCRIPTIONS OF THE DRAWINGS

DETAILED DESCRIPTIONS

Figure 1:
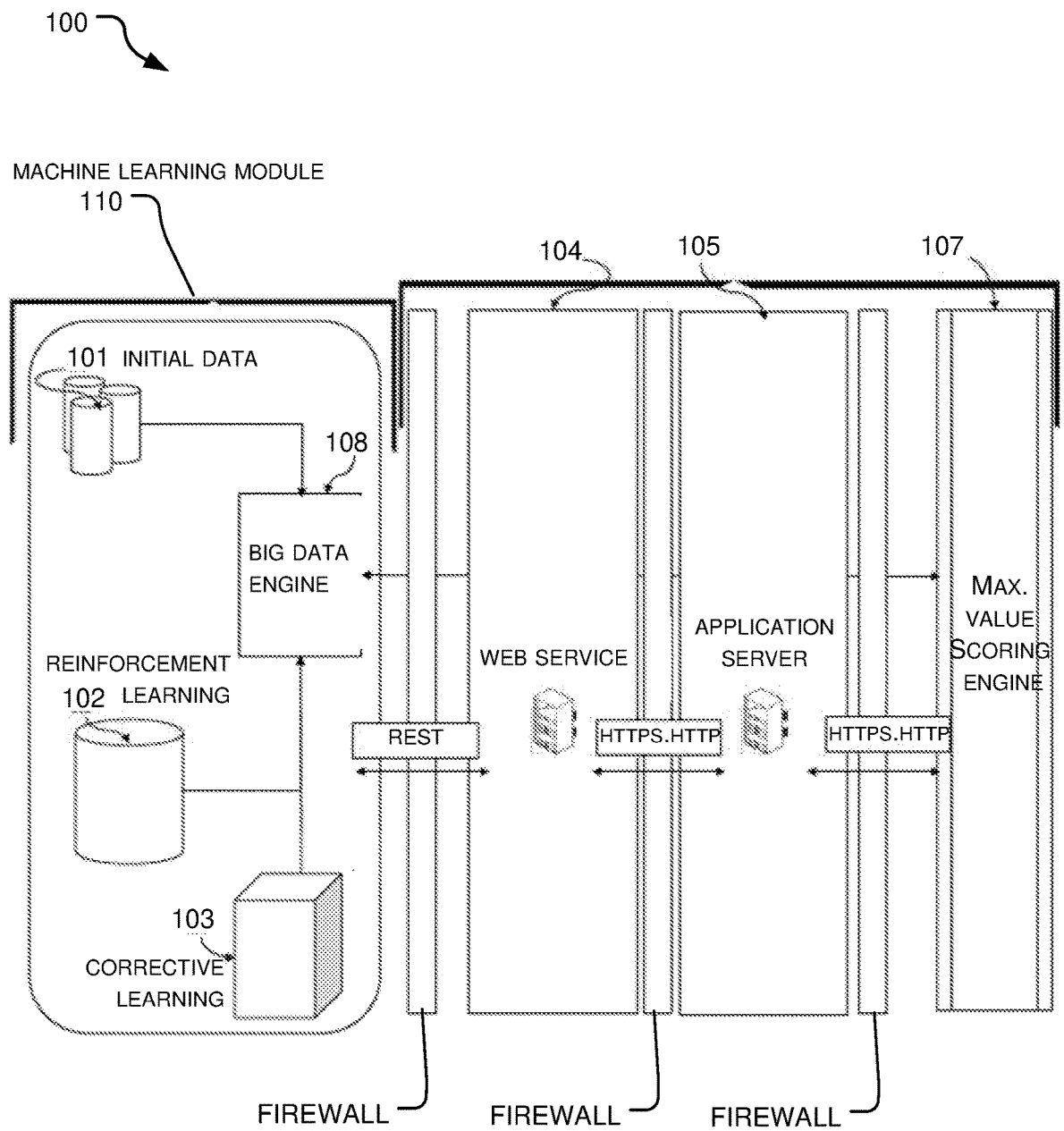
FIG. 1 is a schematic diagram of an example long-term healthcare cost predictions system.

Several costs that have been previously covered by healthcare insurances are now increasingly shifting to the individual as an out-of-pocket cost making it necessary for a model that not only looks at historical data for the medical event occurrence and the possibility of the event resulting in out-of-pocket costs by taking into account the population of plans that are active today, along with the types of provider networks each plans have, the healthcare cost inflators for that region to come up with a more accurate picture of what the healthcare costs could be over longer periods of time, as in over entire retirement or over the entire life spans of the individuals within a family.

The disclosed technology provides individuals and families with a personalized healthcare cost forecast based on comprehensive healthcare expense data at a population level, real-time sampling, modeling, and analysis to create a forecast both at an individual and a family level over their lifetime, pre-retirement and post-retirement, as well as during Medicare. The technology uses several data points that show actual out-of-pocket costs due to various events for different individuals with different plans over several years to create a model that creates several thousand future trajectories of an individual's healthcare costs and then identifies the most probable trajectories within these trajectories to create a more accurate representation of the costs. The longitudinal forecast over long periods of time is accomplished by trajectory stitching, wherein long-term trajectories are created as a combination of several short term trajectories.

While intuitively it may seem that only individual characteristics contribute to healthcare costs, structural similarities and contexts (e.g., health profile, where the individual lives, age, gender, a current healthcare plan, etc.) are as significant as the individual health profile. The disclosed technology takes into account the context of the individual to create a contextual map of the individual and similarity between other individuals and associated cost trajectories that embeds these contextual relationships.

By combining the ability to process large amounts of data, modeling the data with prior knowledge embedded in the data and through continuous reinforcement learning to improve the forecasting engine, the disclosed technology builds a long-term forecasting engine that takes into account several factors at a macro level and at a micro/individual level, and continuously learns to improve its forecast.

Healthcare expenditures of an individual are influenced by several factors which can be grouped into at least four main categories (and other categories are contemplated):

1. Location Factors: where an individual lives, available healthcare services, costs of such healthcare services at that location, inflationary factors specific to the location, the density of the healthcare providers in that region, presence or absence of any particular kind of healthcare facility.

2. Individual/Consumptive Factors: an individual health profile, chronic conditions, age, gender, healthcare protocols that prescribe specific diagnostic tests at different ages for a specific gender.

3. Plan Factors: The various attributes of a plan that result in expenditures for the individual when healthcare services are consumed, the quality of the healthcare network, and the density of the in-network healthcare network for various healthcare services in different geographical areas. Within several plans, few plans could have a better negotiated rate for a particular service resulting in different out-of-pocket costs for the same service.

4. Regulatory Factors: Premium determination for various income levels, premium inflation associated with income levels, changes to drug subsidies, which can change based on economic conditions and the state of the government budget, etc.

Each individual is affected by the factors above and the disclosed technology generates future expense trajectories based on all of these factors. The future expense trajectories are compared with several existing trajectories from the data that has been mined to identify the most probable trajectories that might apply to a particular family unit based on predetermined criteria (e.g., age, gender, where the family lives, and family composition).

The disclosed technology includes a cognitive application that has features similar to human cognition, such as memory, reasoning, and learning to address the problem of prediction. The cognitive application yields an accurate and dynamic model that constantly learns to alter the memory based on new data and reason based on knowledge derived from the data. A memory component of the cognitive application constitutes a static database module which stores data for all healthcare expenditures related to individuals over several years.

A reasoning component constitutes the computer modeling module which reasons over the data within the static database module to create a hierarchical graph structure with a knowledge graph at the top most level of the hierarchy that is a synthesis of the broader data. Using a synthesized knowledge graph, the reasoning component generates different trajectories for an individual over time and eliminates trajectories that are not feasible and retains trajectories that are feasible.

A belief network which facilitates the reasoning is repeatedly improved and updated through new data that is obtained. The new data reflects a current situation on how different contextual factors (e.g., location, age, and healthcare provider interaction which changes from time to time due to new treatment protocols), and thus, cost, allow the big data engine to incorporate the impact of these factors to the cost trajectories.

The disclosed technology includes methods used with hardware, including servers on the cloud in a virtualized environment. Large graphs with billions of nodes and relationships are processed in real-time. Sub-graphs or portions of graphs are extracted and compared. The sub-graphs or portions of graphs can have several hundred nodes. The methods are extremely time consuming, involve computationally intensive processes, and cannot be performed by humans.

FIG. 1 is a schematic diagram 100 of an example long-term healthcare cost predictions system. A machine learning module 110 is shown, which includes a big data engine 108 coupled to an initial data module 101, a reinforcement learning module 102, and a corrective learning module 103. The big data engine 108 receives user data and forecasts lifetime expenditures. The initial data module 101, consists of data regarding healthcare services consumed by an individual, the reasons for the service consumption and the cost of the service to the various parties, namely, the individual, and the insurance and the discounts provided by the healthcare provider. The machine learning module 110 processes this data using big data processing techniques that takes the healthcare service consumption and cost data and converts this data into a series of graphs using different deep learning techniques that condense these multiple features into higher order features. The reinforcement learning module 102, uses current data of healthcare service consumption and from time to time adjusts the predictive value of the healthcare costs prediction by comparing them with the actual costs and values. Deep learning, which mirrors human intelligence from time to time, acquires biases that need to be corrected which is then tweaked through a corrective learning module 103. Both the reinforcement learning module 102 and the corrective learning module 103 will update the high level knowledge graph that is created from the series of deep learning activities on the event data to give a more updated predictive model that can improve the predictive capability by ensuring that inflationary factors, plan factors and location factors that change with time and influence healthcare costs are incorporated into the model.

The machine learning module 110 uses a web service 104, accessible via one or more application server computers 105 (or, referred to as an "application server"). In implementations where there is more than one application server, the application servers can be distributed across multiple locations. It is contemplated that each application server can be one or more computers.

An individual accesses a web service 104, through a personal computer or mobile application, that is in communication with the application server 105 through a protected service (e.g., a firewall). The application server 105 communicates with a real-time value scoring engine 107. As seen in FIG. 1, the big data engine 108 and the real-time value scoring engine 107 are in communication through a protected service. The protected service is a user authentication service that ensures that only subscribed users or individuals have access to a representational state transfer (REST) interface. The REST interface is an architectural principle of the web and ensures that the client calling the service doesn't need to know anything about the structure of the Web Service. The REST interface focuses on the interactions between data elements for the web service. The function of the protected service is to provide access control and to ensure only subscribers who are eligible to access the web service are provided with the output.

The communication between the big data engine 108 and the user interface (not shown) happens through a web service layer 104, an application server 105, and a value scoring engine 107. The user input is provided the web service 104 which communicates with the big data engine 108 through a web service 104.

The application server module 104 facilitates the interaction between the user interface and the big data engine 108. The communication between the application server 105, web service 104 and the value scoring engine 107, which is a module implemented on top of the application server 105, occurs via the https (secure http) protocol.

Figure 2:
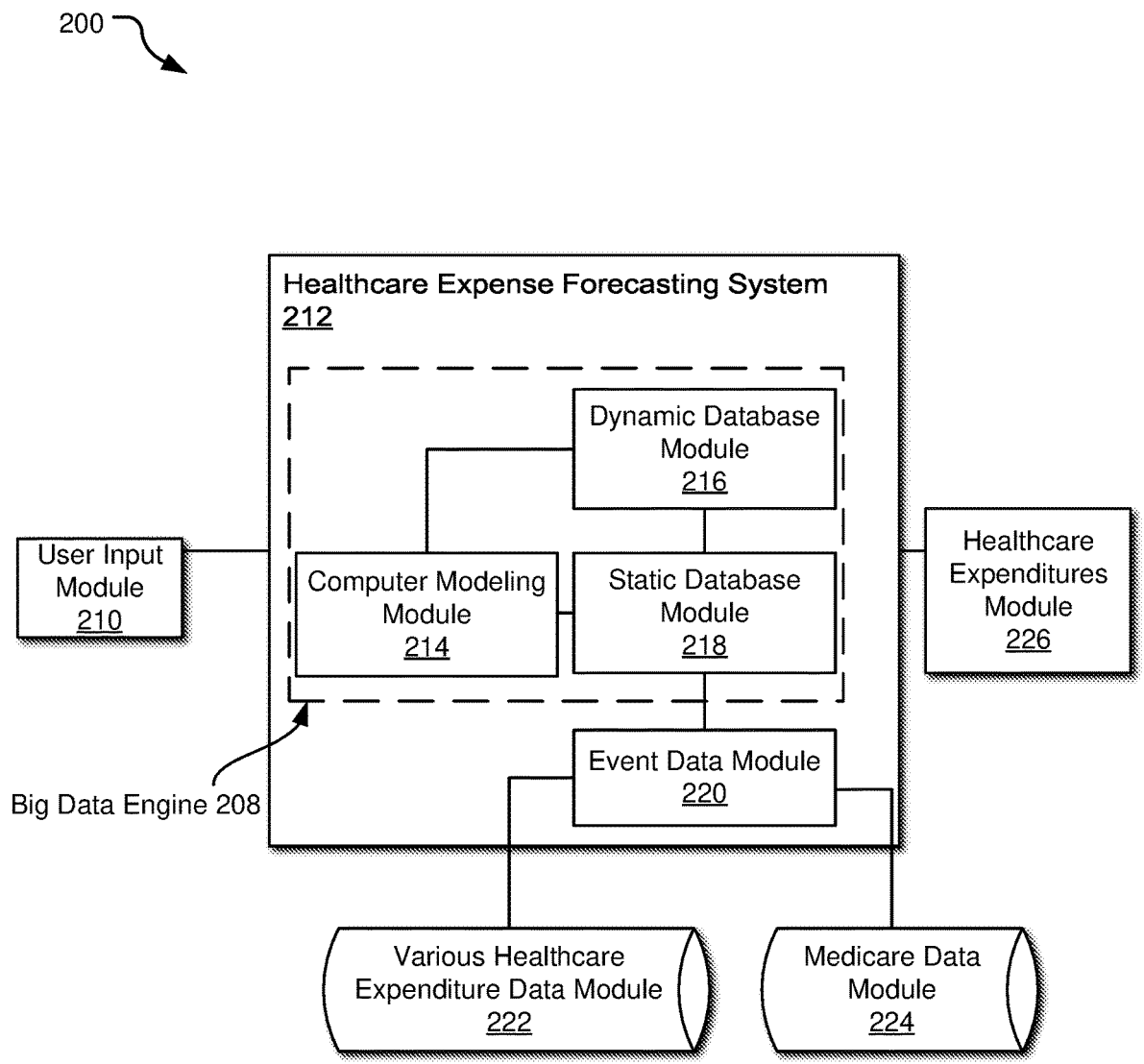
FIG. 2 is a schematic diagram for an example healthcare expeditures system.

FIG. 2 is a schematic diagram 200 for an example healthcare expeditures system. In FIG. 2, the big data engine shown previously in FIG. 1 is shown, which includes three modules and the initial data and reinforcement data combined into an event data module which receives event data from two other source modules. The event data is captured for several individuals. Specifically, an individual can enter user input into a user input module 210 for use in a big data engine 208 located in a healthcare expense forecasting system 212 in a central computing device (not shown). The user input module 210 enables the big data engine 208 to create a context for the individual in terms of the individual's age, location, health plan, health grade and also will have the ability to take historical explanation of benefits to ascertain a health grade which is a combination of the health conditions that an individual may have as well as the different interactions the individual has with healthcare providers. The big data engine 208 analyzes large amounts of data collected, which generates large graphs requiring special processing techniques. The large graphs result in a healthcare expenditures module 226, which projects healthcare expenditures over an individual's lifetime.

The healthcare expense forecasting system 212 models progression of lifetime healthcare expenses, including healthcare events resulting in an out-of-pocket expenditure per a given healthcare plan, wherein each healthcare event is associated with a group of healthcare events. In some implementations, out-of-pocket expenditures are events caused by at least one of a chronic condition and an infectious disease. A causal condition of a healthcare event could persist over longer periods resulting in recurring expenditures over a longer period of time. The causal condition is a chronic condition. A chronic condition may include, for example, a predetermined group of diseases. such as diabetes, renal disease, pre-diabetes etc.

Each group of healthcare events is associated with different sets of certainty with different groups of individuals. The healthcare expense forecasting system 212 includes a computer modeling module 214, a dynamic database module 216, a static database module 218, and an event data module 220.

A central computing device communicates with healthcare event data generation sources. The event data module 220 collects data from events happening within the healthcare domain. These events can be healthcare service consumption events for different individuals (e.g., individuals across the United States) from modules outside the big data engine (e.g., a various healthcare expenditure data module 222 and a Medicare data module 224.) The data collected from the event data module 220, which includes data related out-of-pocket expenditures, plan profiles, and event and subevent groups that categorizes individuals, is stored in a graphical structure (shown and described in FIG. 3) in the static database module 218 in the central computing device. In some implementations, the healthcare event data comprises at least one of susceptible individuals, individuals given therapeutic treatment, individuals treated prophylactically, individuals given no treatment, cumulative number of total individuals with the disease, cumulative number of action taken at early stage, cumulative number of treated individuals with no action taken at early stage, cumulative number of hospitalized individuals with no action taken, cumulative number of hospitalized individuals with action taken at an early stage, days of hospital stay per individual for individuals with no action taken at early stage, and days of hospital stay per individual for individuals with some action taken at early stage.

In one implementation, the static database module comprises information about individuals in a predetermined population, including at least one of age, race, sex, location, healthcare plan type, prevalence of diseases, and expenditure causing events. The static database module may be a layered graph that includes temporal event data at an individual level which is aggregated, and the highest level graph representing the aggregated causal graph as a Bayesian Belief network. The static database module may be represented as a graph of vertices and edges with several layers of abstractions, and wherein the static database module uses machine learning techniques to identify similar paths. The static database module may be updated periodically to revise the beliefs in the top level causal Bayesian Belief network. The static database module comprises information about the cost variabilities in treatment based on personal factors. The data in the static database module is updated on a periodic basis from time to time through historical claim and plan profile data to update the belief network and take into account the location specific changes, provider specific changes etc.

The dynamic database module 216 creates sequential layers of graphs that represents information after combining it with data in the static database module 218. The structure obtained provides a contextual representation which has trajectories that encapsulate the health and healthcare costs of the individual over time. The dynamic database module 216 also creates a belief network that synthesizes the event data and identifies causal relationships between the plan factors, health factors and location factors and the individual trajectories over time. Thus, the dynamic database module 216 creates a knowledge domain of the different characterstics of an individual, taking into consideration individual interactions and how such interactions relate to the health and cost progression over time. The dynamic database module 216 also creates classes of individuals who are similar in all respects in terms of their demographic factors, health conditions, and plan factors. The dynamic database module 216 requires significant computing power as it traverses graphs that have several billion nodes and uses specialized GPU machines. The dynamic database module 216 dynamically generates data that depicts different future expenditures over a life span given the predetermined set of criteria and stores the data in a graphical structure as a series of paths over nodes representing individuals and year time periods.

The data in the dynamic database module is simulated over several thousand permutations to create potential future trajectories that an individual or group of individuals may traverse over a lifetime. The data in the dynamic database module is obtained by various individual trajectories based on correlations between an individual's current age and surviving age. For example, an individual who is currently at age (25) and given a life expectancy of age (92) we will have several data points that accurately describes the entire lifetime costs of this individual. There is a known credible group of 80 year olds for the next 12 years with known cost values. There is a known credible group of 70 year olds for the next 22 years. There is a known credible group of 60 years olds for the next 32 years, etc. . . . . . Stitching the cohorts together provides a lifetime trajectory of the 25 year old individual without data limitations. In this context, a cohort will be a group of people based on age, location, and other individual factors who represent the same profile as the individual for whom a prediction is being made. The data in the dynamic database module is a series of paths through a graph and set of nodes representing the expenditures for each year.

The computer modeling module 214 generates the most likely set of future expenditures using data as paths in the dynamic database module 216 and hierarchical layered graphs in the static database module 218. The computer modeling module 214 takes the stored data in the static database component 218 and creates a synthesized representation and updates higher level graphs in the static database module. The computer modeling module creates various trajectories as paths in a graph and stores the paths in the dynamic database module.

The computer modeling module 214 traverses an event graph at lower layers to create higher level representations of event a embedding it with context. The highest layer of such a graph becomes a synthesized knowledge graph. The synthesized knowledge graph is then utilized by the computer modeling module 214 to further generate different trajectories of healthcare projections based on the user input. To create these trajectories, the computer modeling module 214 uses classes of individuals that are similar across ages and then stitches the trajectories to get a trajectory that encompasses the entire lifespan. From these several thousand probable trajectories, the most probable trajectory is chosen, along with the limits to provide a prediction.

In one implementation, the computer modeling module is configured to create enriched hierarchical layered graphs in the static database component with a highest level graph being a Bayesian Belief network. The computer modeling module computes several thousand paths for a given individual using the data from the Bayesian Belief network.

In some implementations, an individual can request recommendations based on modified output from the healthcare expenditures module 226. The user inputs and requests for outputs can occur in real-time. A set of interactions resulting from the disclosed technology can range from one to one million for a particular consumer.

Figure 3:
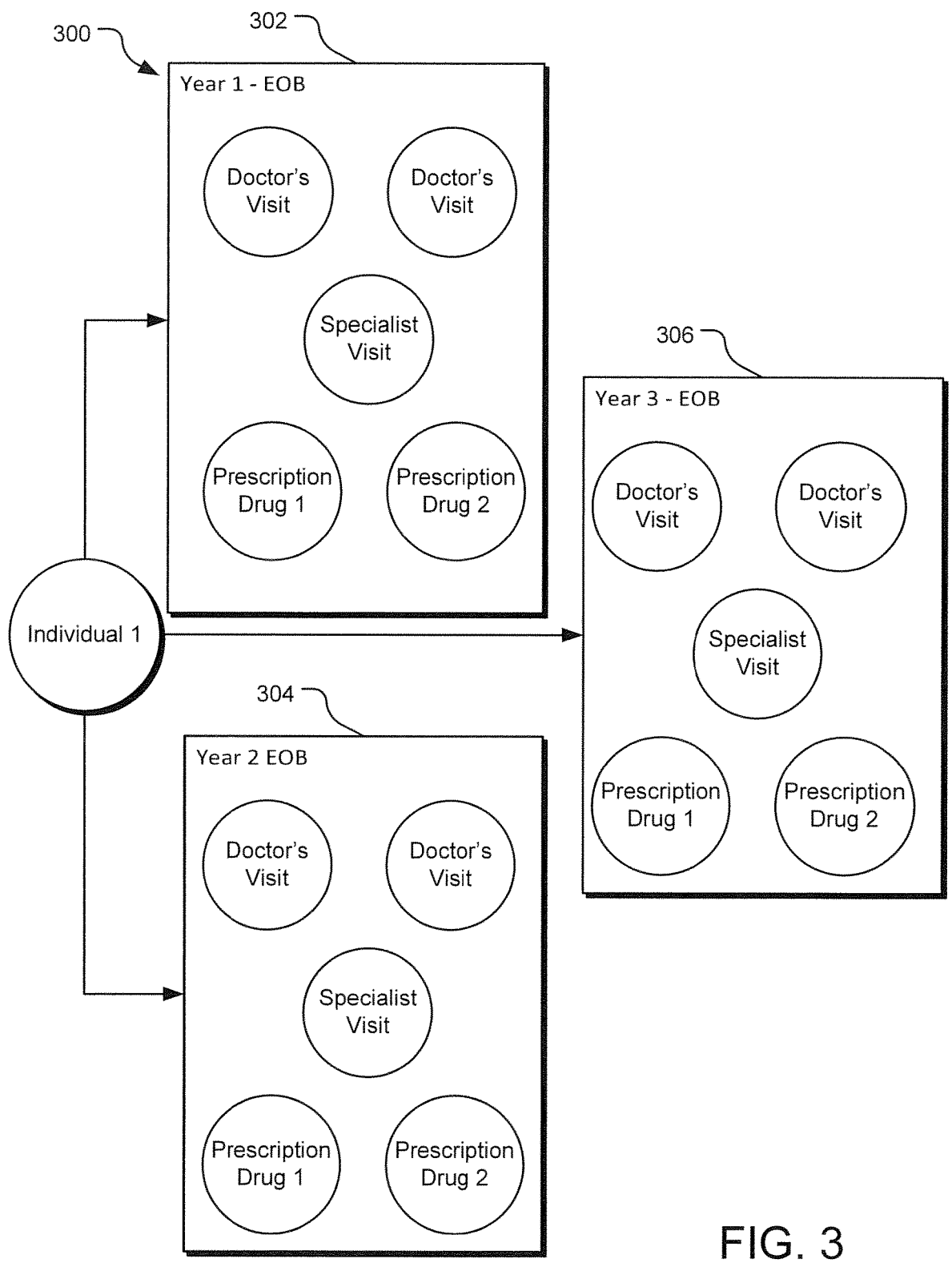
FIG. 3 is a schematic diagram of an example usage profile.

FIG. 3 is a schematic diagram 300 for an example usage profile. Specifically, FIG. 3 shows a representation of the event data or health care service usage by a single individual. After the individual communicates with a graphical user interface and gains access to a web service, a usage profile for an individual (or subscriber) is collected over multiple years (e.g., for 10 years). In one implementation, as shown in FIG. 3, data collected for an Individual 1 for a Year 1 in EOB 302 includes data for two doctor's visits, one specialist visit, and two prescription drugs for Individual 1, which may be derived from an Explanation of Benefits (EOB). Similarly, data collected for a Year 2 shown in EOB 304 includes data for two doctor's visits, one specialist visit, and two prescription drugs for Individual 1, and data collected for a Year 3 shown in EOB 306 includes data for two doctor's visits, one specialist visit, and two prescription drugs for Individual 1.

The big data engine generates a usage profile and proceeds to calculate the value vector ranges based on the usage profile. The individual can review the value vector ranges and make changes to inputs if deemed necessary. Due to the real-time interaction, these operations can occur multiple times before the individual decides on the final output.

Figure 4:
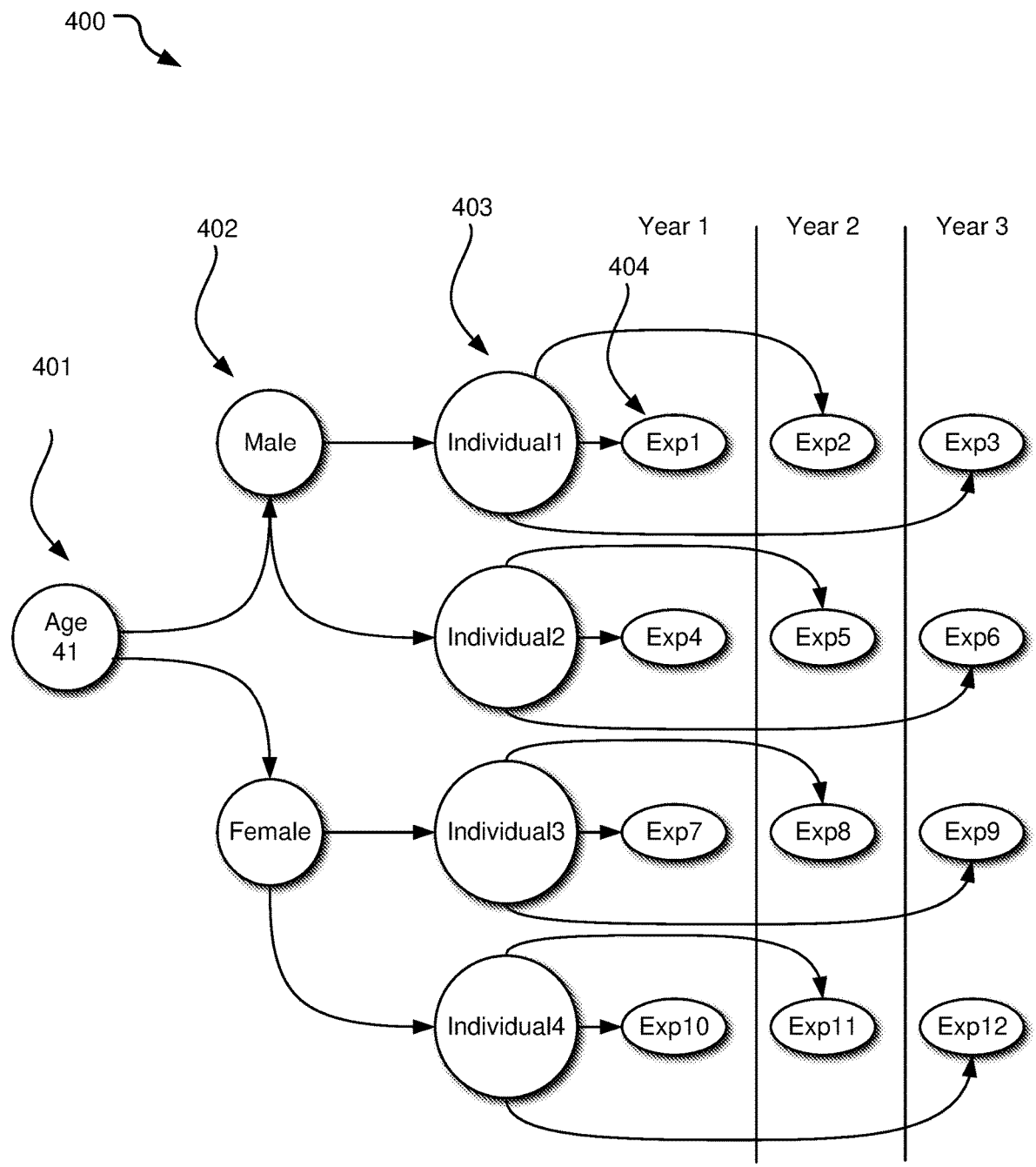
FIG. 4 is a schematic diagram for an example contextual representation of healthcare service consumption data with personal factors.

FIG. 4 is a schematic diagram 400 for an example contextual representation of healthcare service consumption data with personal factors. Specifically, the data generated in FIG. 3 is used with a grouping of different individuals who have similar health and similar personal factors. For example, these personal factors can include location, healthcare service consumption, plan information, etc., by using structural information stored within a graph by virtue of relationships between the nodes. FIG. 4 connects various individual usages and connects the usages with shared personal factors that represents a context.

As shown in FIG. 4, a first set of data includes a personal factor 401 for the individual (e.g., age 41). A second set of data includes a second personal factor 402 for the individual (e.g., gender). In other implementations, there could be other personal factors 403 (e.g., health grade, income level, etc.). Multiple expenditures (e.g., Exp 1 404) are shown occurring over multiples years (e.g., Years 1, 2, and 3) and represent aggregated expenses of healthcare services for each year. There could be several expenditure aggregates based on types of healthcare services. While costs are an important aggregated information, several aggregates including costs are also derived in the disclosed technology. The healthcare service consumption and the associated costs over the years are what we call the trajectory.

Figure 5:
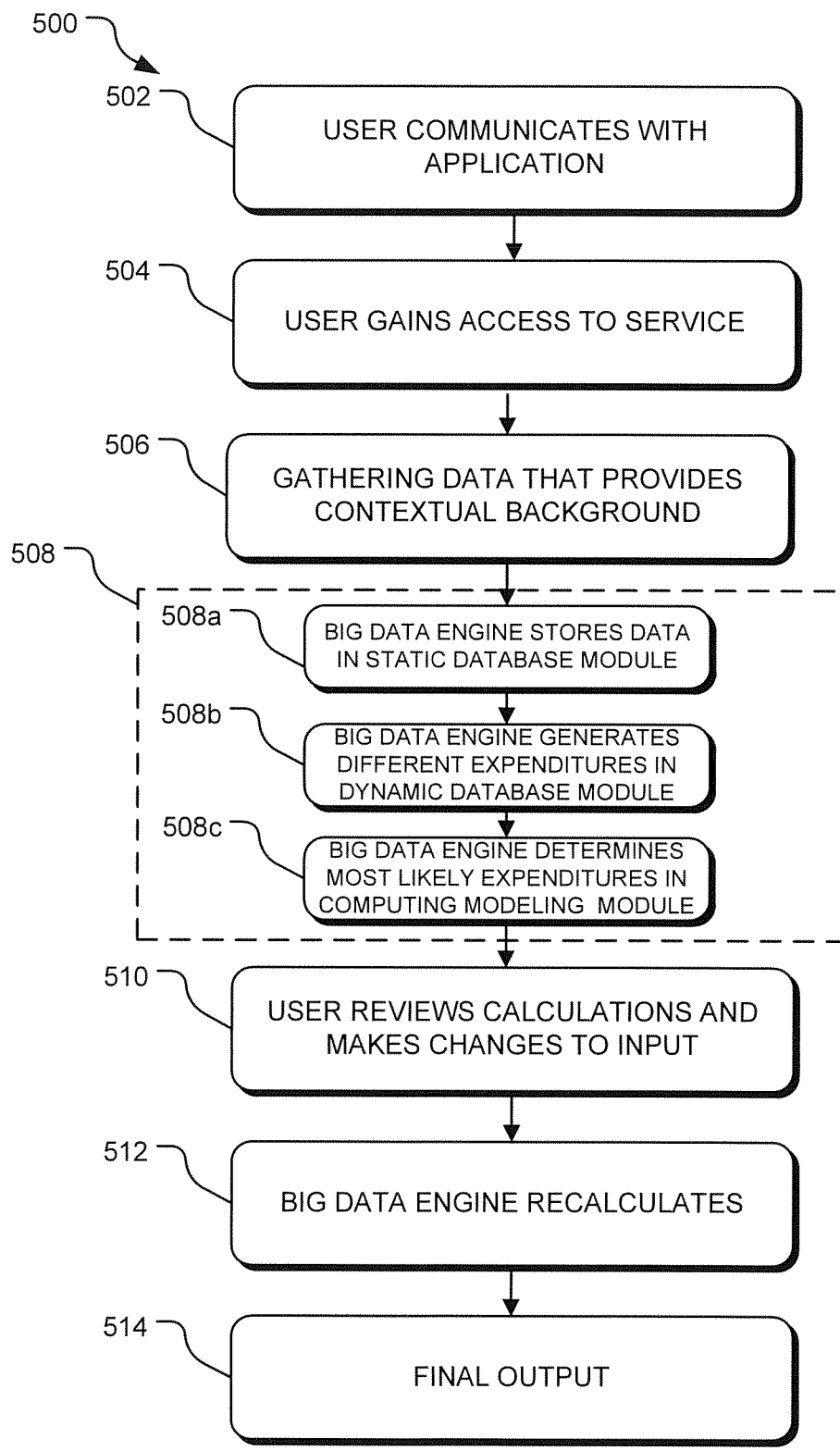
FIG. 5 is example operations for the representation of the event data in a semantic network that connects the event data with an individual and an individual's context.

FIG. 5 is example operations 500 for representation of the event data in a semantic network that connects event data with an individual and the individual's context. FIG. 5 shows the interaction of a user with the healthcare prediction system in FIG. 1. In an operation 502, an individual communicates with an application through a user interface that can allow the individual to register and gain access to a web service.

In an operation 504, the individual gains access to the web service through a protected service which authenticates if the individual (or applicant) calling the web service is eligible to get the information. The authentication is established between the applicant and the web service, which is reviewed every year to see if all applicants are still eligible for the access.

Figure 6:
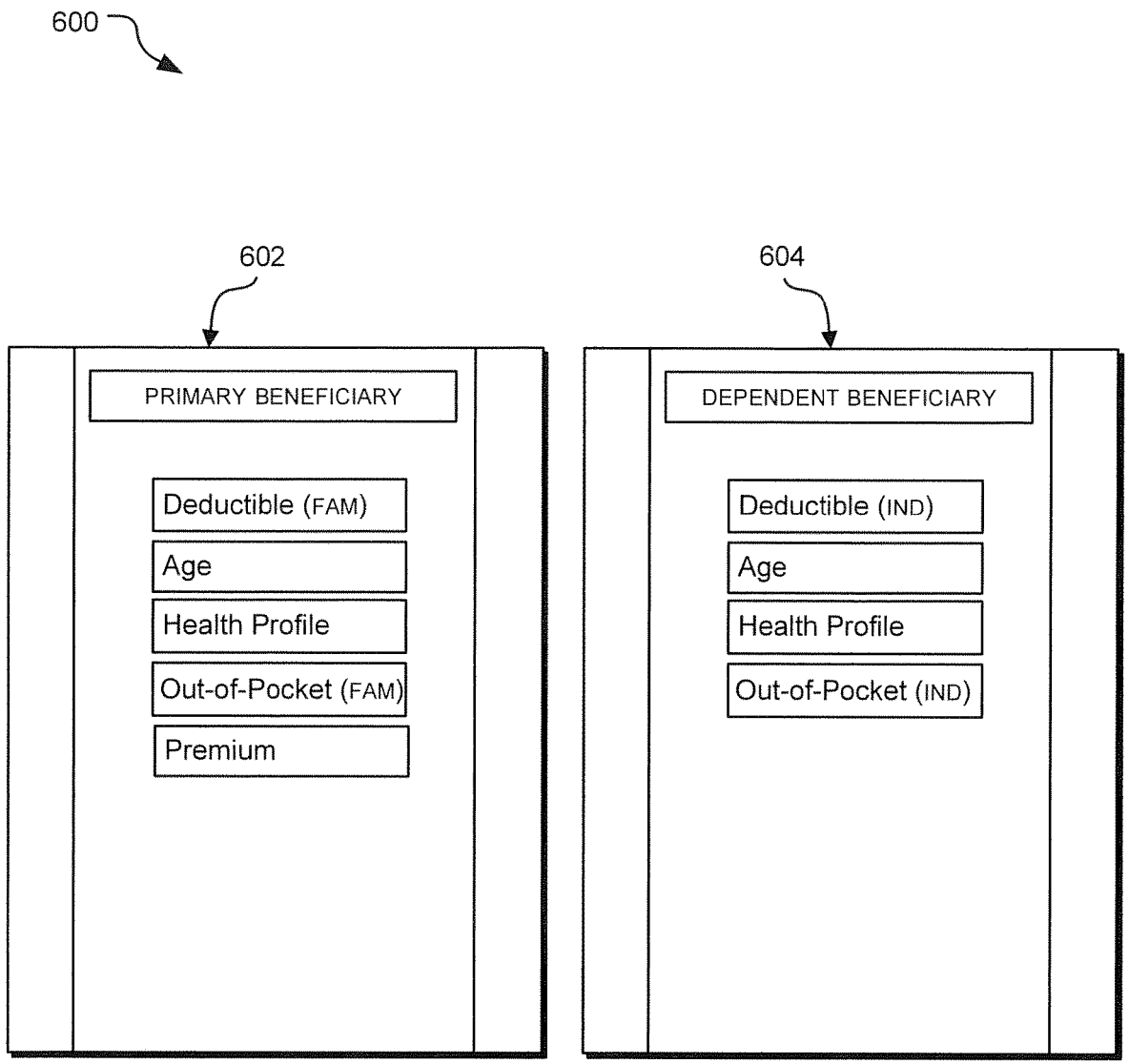
FIG. 6 is a schematic diagram of an example consumer interface.

An operation 506 gathers data to provide contextual background through individual user input forms (shown and described in FIG. 6). In an operation 508, modules in the big data engine store data gathered in operation 506 and perform calculations on the data. Specifically, in an operation 508a, the big data engine stores a plurality of healthcare event data accessed from healthcare event data generation sources, wherein each healthcare event is associated with a group of healthcare events, and wherein each group of healthcare events is associated with different sets of certainty with different groups of individuals in hierarchical layered graphs in a static database module in a central computing device. In an operation 508b, the big data engine generates data dynamically that depicts different future expenditures over a lifespan from a current year based on the healthcare event data with a dynamic database module. In an operation 508c, the big data engine determines a most likely set of future expenditures using the generated data in the dynamic database module with a computer modeling module.

In an operation 510, the individual reviews the calculated output from operations 508a-c provided by the big data engine and decides whether to modify some of the consumption values based on past experiences previously not provided in the user input, as well as modify other factors provided as part of the input. For example, if the big data engine provides four diagnostic visits as part of its output in justification of the predicted cost, and the individual knows by personal experience that he has to avail six diagnostic visits, the individual will then provide an updated consumption value of six visits. The modified input is used to reassess the trajectory choice and may lead to the choice of a different individual trajectory and hence a modified family trajectory. Another example may be the individual adding and removing family members on a plan to evaluate the cost impact if an adult or dependent continues within the plan or chooses a different plan. A third example may be the individual making changes to the health factors, demographic factors, or plan factors (e.g., deductible limits, etc.) which may alter cost trajectories of the individuals and families.

In an operation 512, the big data engine recalculates the healthcare expense trajectories in the light of the new information from individual's modifications using the static database module, the dynamic database module, and the computer modeling module. The big data engine provides a revised most probable trajectory for the entire family and a revised healthcare service consumption for the different healthcare service categories.

FIG. 6 illustrates an example consumer interface 600 in the disclosed technology (or the user input module 210 described in FIG. 2). A user input screen 602 is shown on the consumer interface 600. An individual can provide data about the individual (shown as "primary beneficiary") and the individual's family, such as a combination of personal information, health information, and plan information (e.g., deductible, age, health profile, out-of-pocket examples, premium, etc.) in the user input screen 602. An individual can provide similar data for a "dependent beneficiary" in user input screen 604.

The static database component has a belief network that has knowledge encapsulated in a probabilistic model that can be used to determine how a particular individual's health trajectory will be in the future, or probabilistically assess several different futures. As provided above, the data obtained from the user input screens in the consumer interface provides contextual background provides data for use in example operations 500 for representation of the event data in a semantic network that connects event data with an individual and the individual's context, specifically operation 506. This data helps identify how a particular individual fits into the knowledge domain and then generates possible future expenditures for all the individuals in a family. These future expenditures are then condensed into the most probable future expenditures and then that trajectory is extracted to determine the healthcare expenses.

Figure 7:
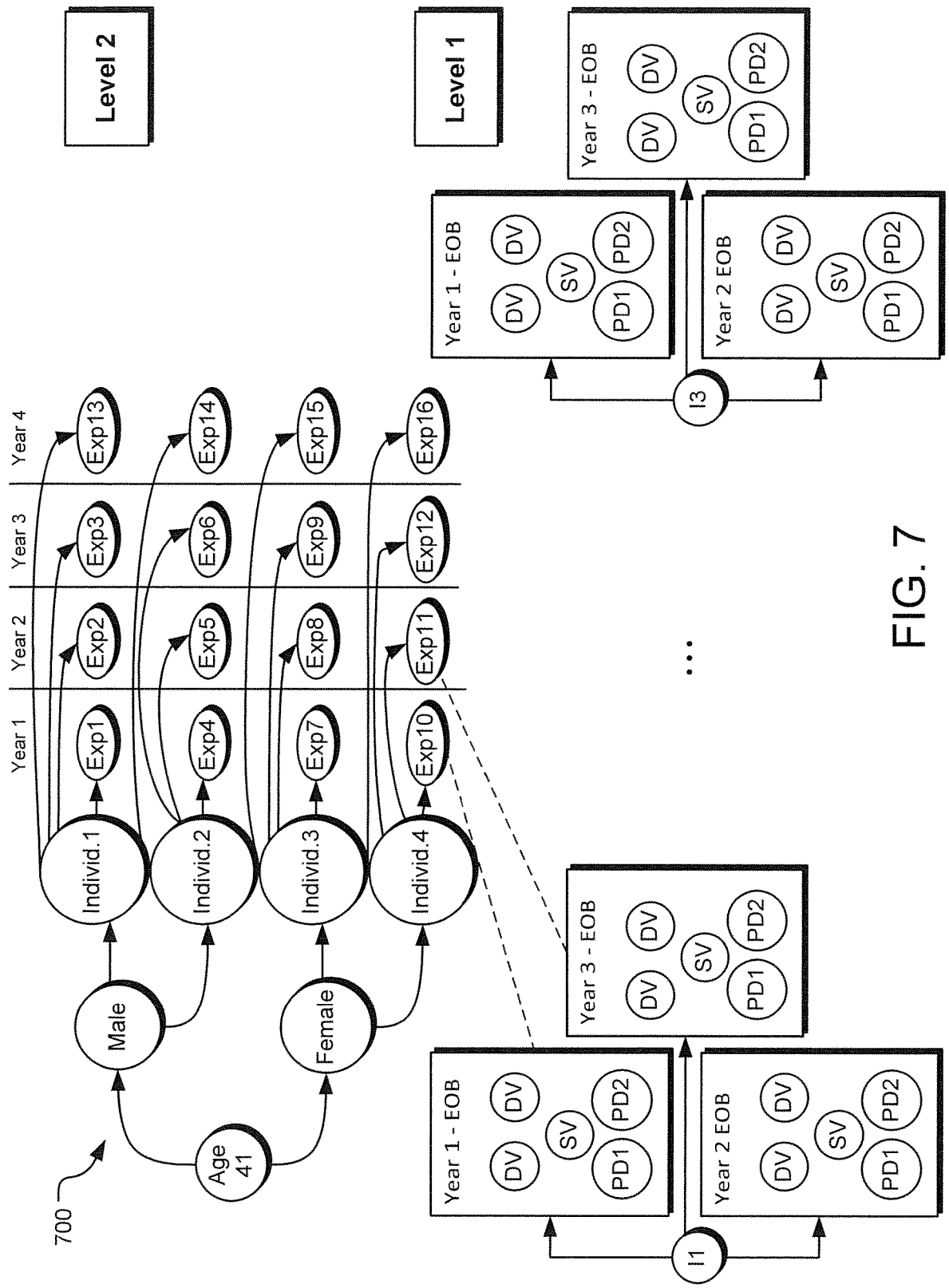
FIG. 7 is a schematic diagram of example individual healthcare expenditure data.

FIG. 7 a schematic diagram 700 of example individual healthcare expenditure data. The individual usage profile in FIG. 3 is used to derive the contextual representation of all individuals in FIG. 4. Specifically, example event data and contextualization of event data for individuals in a graphical format and derivation of a Level 2 graph using statistical summaries from the event data and associating contextual factors of numerous individuals are shown.

The data is represented in a semantic network in Level 1 and after traversing the Level 1 network creates a Level 2 semantic network where individuals are all connected by a shared set of personal factors, such as age, gender, and the healthcare service consumption is aggregated. The Level 1 network comprises of an individual's EOBs for each year (as shown and described in FIG. 3). Within the EOB, there is information pertaining to the doctor visits (DV), specialist visits (SV), prescription drugs (PD1 and PD2). Each visit may have information pertaining to a particular visit that is not shown in the diagram. Three years are shown (I1 to I3). This data is then converted into a Level 2 network where the different individuals are connected by common characteristics such as Age (41) and Gender (Male or Female) and the expenditures for each year is calculated as Exp1, Exp2, Exp3, etc. The actual graph is significantly more complex when all the contextual factors are included, creating a gigantic graph with several million nodes connected by several million connections with each node and connection having various properties.

Figure 8:
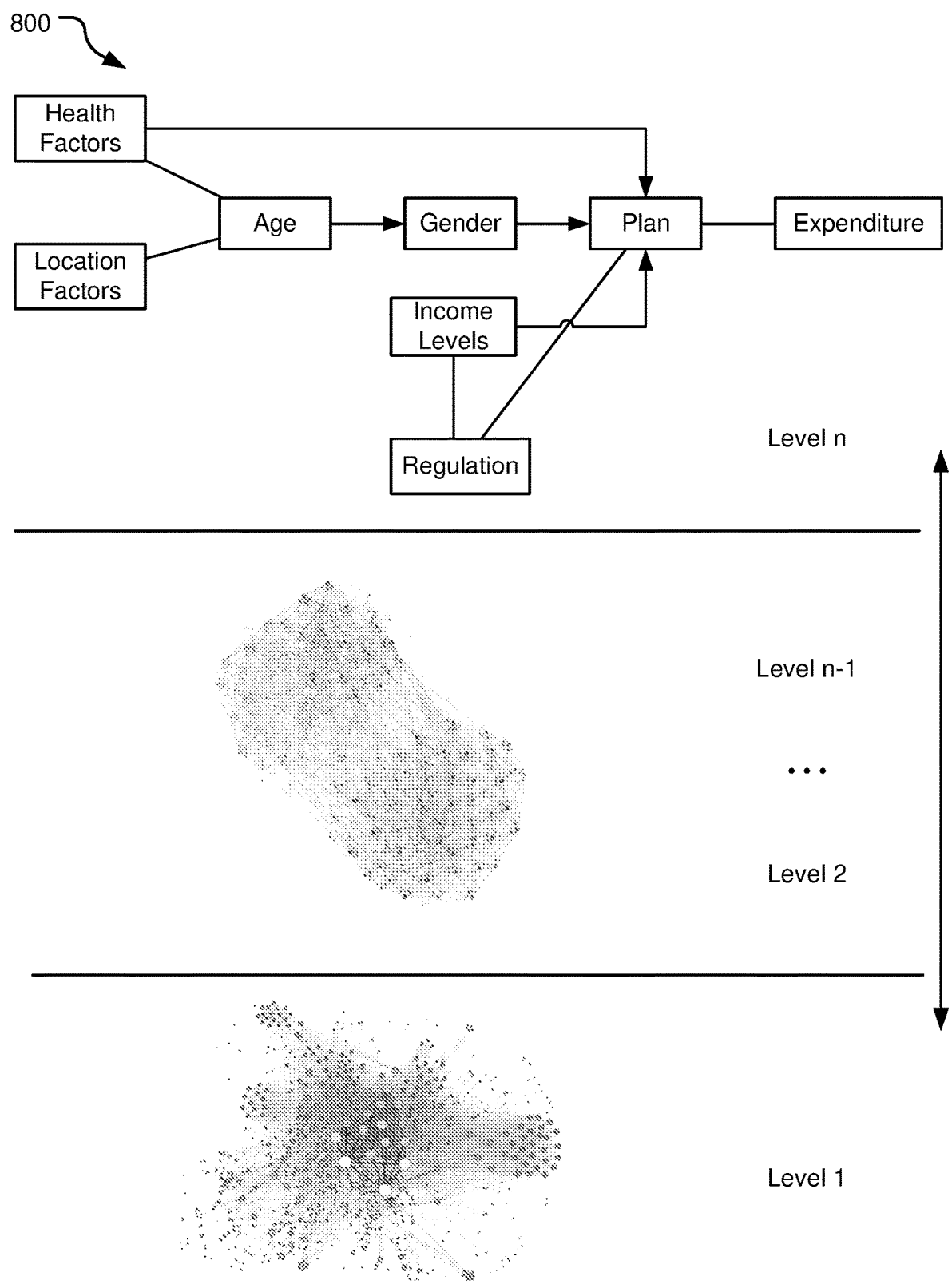
FIG. 8 is a schematic diagram of an example graph layering process.

FIG. 8 illustrates an example graph layering process 800. Compared to FIG. 7 where the individual event data is contextualized into one higher level graph, a high level belief network is obtained and shown in FIG. 8. In the graph layering process 800, several million nodes representing individuals visiting different healthcare providers are shown in the lowest layer Level 1. A synthesized representation of knowledge is obtained from the data in Level 1 is shown at Level n. A final knowledge gaph is generated that synthesizes the data into probabilistic model. The final knowledge graph can be used to generate cost trajectories of an individual, given the individual's personal factors, plan factors, location factors, and regulatory factors.

The lowest layered graph Level 1, is a set of interconnected nodes representing individuals, their demographic factors, their location factors, plan factors and the individual's interaction with healthcare providers. At Level 1, the graph consists of an individual's interaction with the healthcare provider and each interaction is represented as an individual node connected to a healthcare provider node through a relationship. Both nodes and the relationship carries properties that include details about the individual, the provider, the nature of the service provided, the disease and diagnosis etc.

From this lowest layered graph Level 1, other nodes are created from the properties of the individual node to signify demographic factors such as age, and calculated factors such as health grade. The higher level graph Level n is obtained by a statistical traversal of the lowest level graph Level 1 and creation of a second layer graph Level 2 that has the individual situated in the context (interconnected with other nodes) of demographics, location, plan and various interactions with healthcare providers resulting in an out-of-pocket cost for a year.

From these graphs, causal relationships between these variables are determined. In the case of healthcare cost prediction, the dependent variable tobe predicted is a graph that represents the evolution of healthcare expenses over time. This evolution of healthcare expenses over time in the future is what we call as a trajectory. Each trajectory is influenced not only by the individual's health conditions but also the context the individual is situated in such as the individual's plan, age, where the individual lives, income, etc.

Causal relationships can be inferred from the data through hypothesis inference, by transmitting probabilistic information from the data to the various hypothesis. This model is called a Bayesian Belief network, which unlike a rule based model, uses the data to obtain the knowledge. In addition, Bayesian Belief networks also have the capability to incorporate prior expert knowledge through the use of prior and conditional probabilities. With this ability the high level knowledge graph is now able to determine the trajectories of expenses of a given individual given the contextual he or she is situated in. For example, a 30-year old person with diabetes who is in New York, N.Y. and is on regular medication (indicated by regular prescription refill interactions with pharmacy) will have a cost trajectory that may not correspond to the cost trajectory of a person living in Jackson, Wyo. having the same age and has inconsistent prescription refills.

A top level belief network creates a probabilistic causal model that relates the trajectory graph with the individual context determined by the nodes the individual is connected to, with each node signifying a factor (plan, location, demographic, healthcare provider interaction sub-graph). As new data is obtained, the changes in the trajectory relationship with factors such as plan, location, demographics, etc., is automatically updated with a new belief structure that may alter the probabilistic relationships to signify the new reality.

Figure 9:
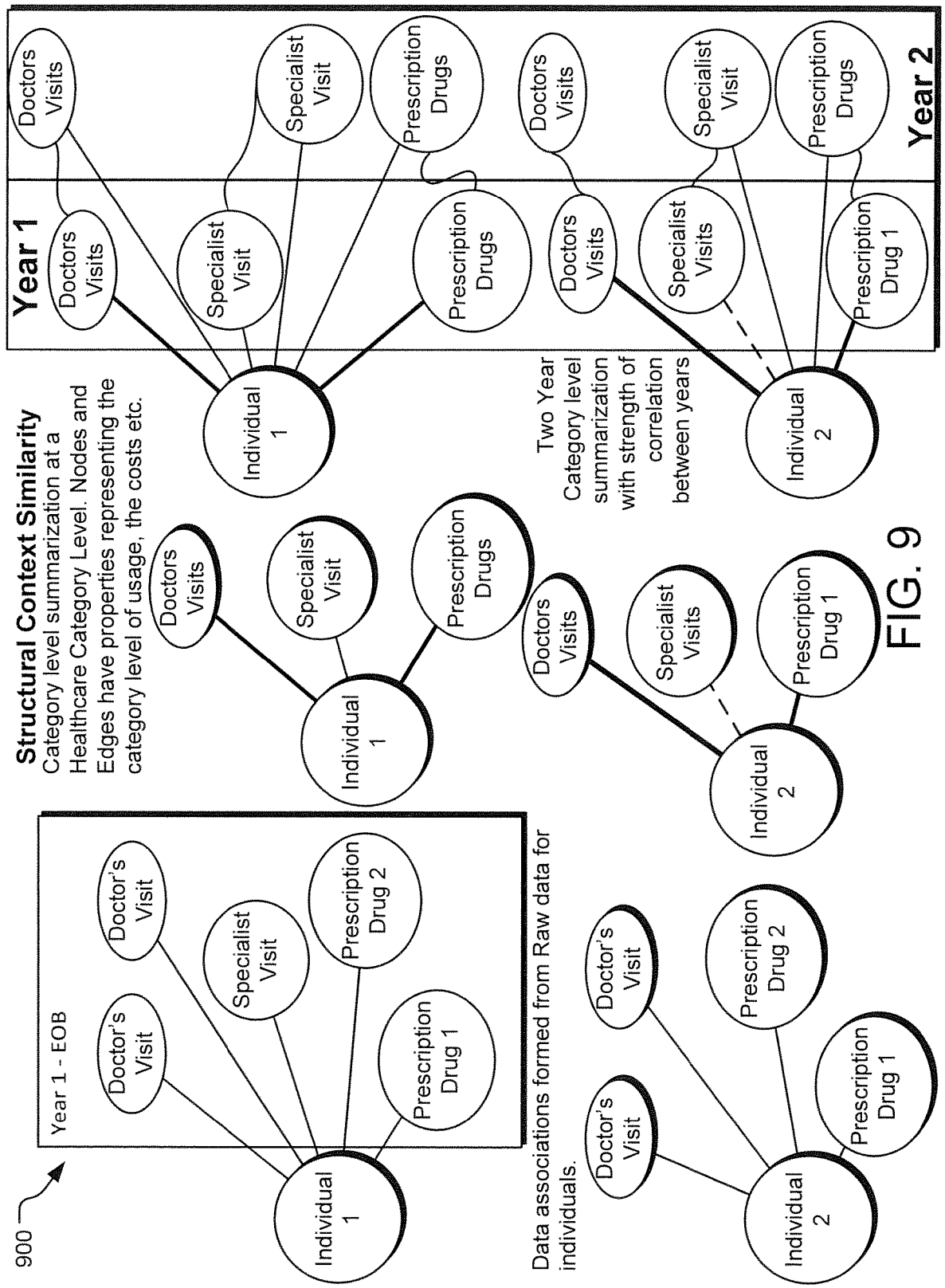
FIG. 9 is a schematic diagram of example structural similarities of different individuals.

FIG. 9 is a schematic diagram 900 of example structural similarities of different individuals which is similar to human cognition where the structure represents context. How the aggregated data is compared by individual variables and by their connections is shown. FIG. 9 illustrates how the big data engine effectively captures the context of an individual based on attributes, such as age and health, and on the interaction the individual has with various healthcare providers 900. The context is represented as a graph/network and two sub-graphs of individuals connected with nodes that represent a healthcare service consumption. Two individuals are then compared based on the similarity of their healthcare service consumption. The graph depicted is a property graph wherein both the node and relationship (the circle and the arrow connecting the circles) both can have properties that can be multi-dimensional.

For example, an individual (node) can have health conditions such as diabetes, end stage renal disease, and the relationship which signifies a single interaction with a healthcare provider (arrow) can have characteristics associated with it, such as the diagnostic codes, procedure codes, and billing codes.

Figure 10:
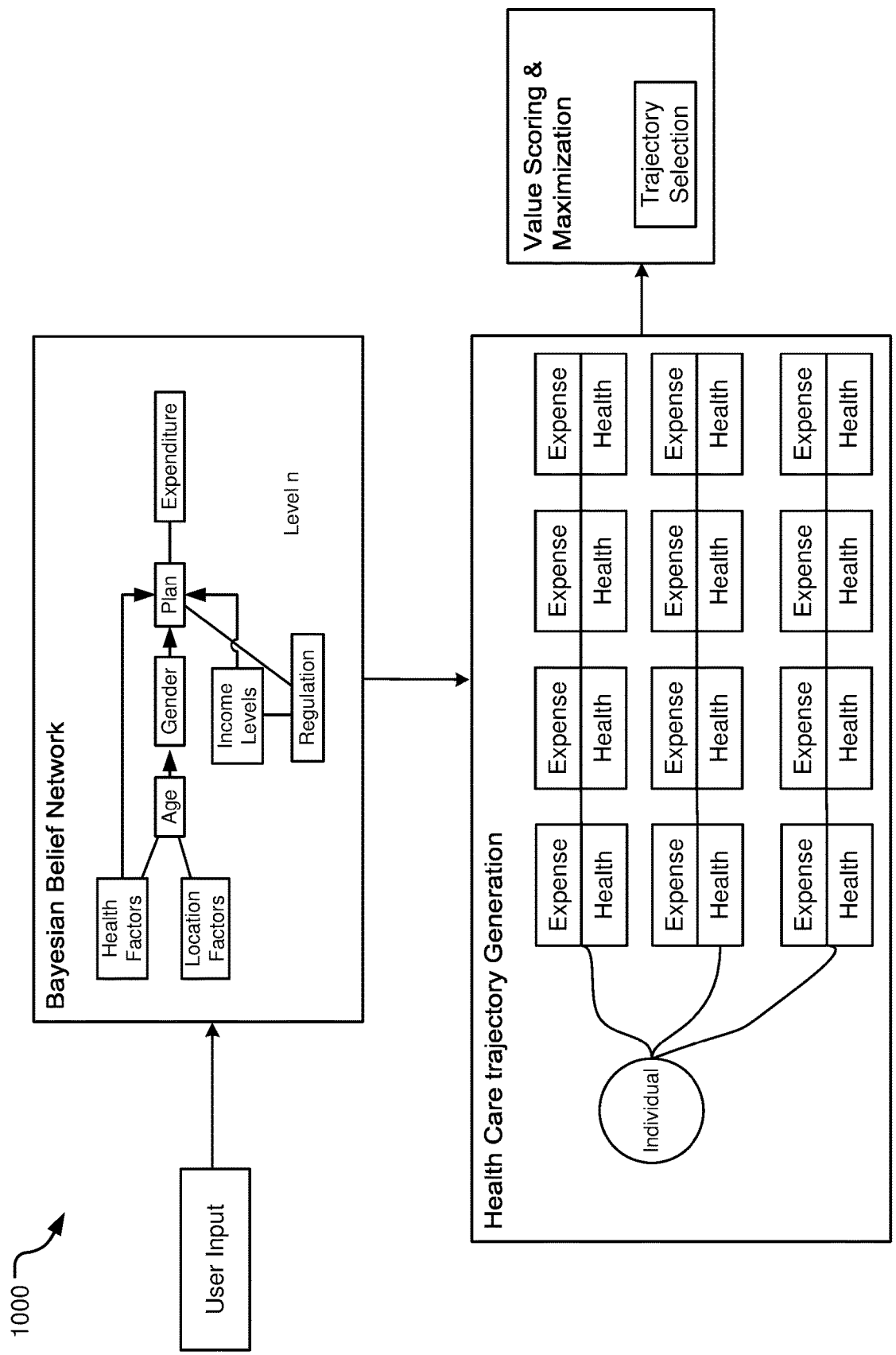
FIG. 10 is a schematic diagram for an example method for generating long term costs and an individual's health changes.

FIG. 10 is a schematic diagram 1000 of example method for generating long term costs and an individual's health changes. In FIG. 10, the belief network in FIG. 8 is used to generate trajectories using the structural similarities in FIG. 9 to provide long term trajectories. Specifically, the diagram shows the input is fed into the Belief network which generates several trajectories which are then evaluated by the value selection and maximization engine to pick the most optimal trajectory for prediction. The method generates long term costs and how an individual's health changes over time. The method includes receiving input data relating to a set of variables, such as health grade, health conditions, out-of-pocket expenditures causing healthcare events related to these conditions, gender, location, out-of-pocket expenditures variation due to the location, income levels and the regulatory impact of income levels on healthcare costs. Potential future trajectories of potential out-of-pocket expenditure events that may occur for each individual in the family unit are estimated. Potential future trajectories are obtained by the use of structural similarity between the individual whose costs have to be predicted and a sub-population who are most similar to the individual and current age matches the future age of the individual. An impact of the out-of-pocket expenditure causing event on the actual out-of-pocket expenditure based on granular plan components for each of the possible future trajectory is determined. A most probable set of future trajectories is determined by use of an automated reasoning engine backed by a belief network. The belief network is updated, or learned, to improve the accuracy of its predictions.

Figure 11:
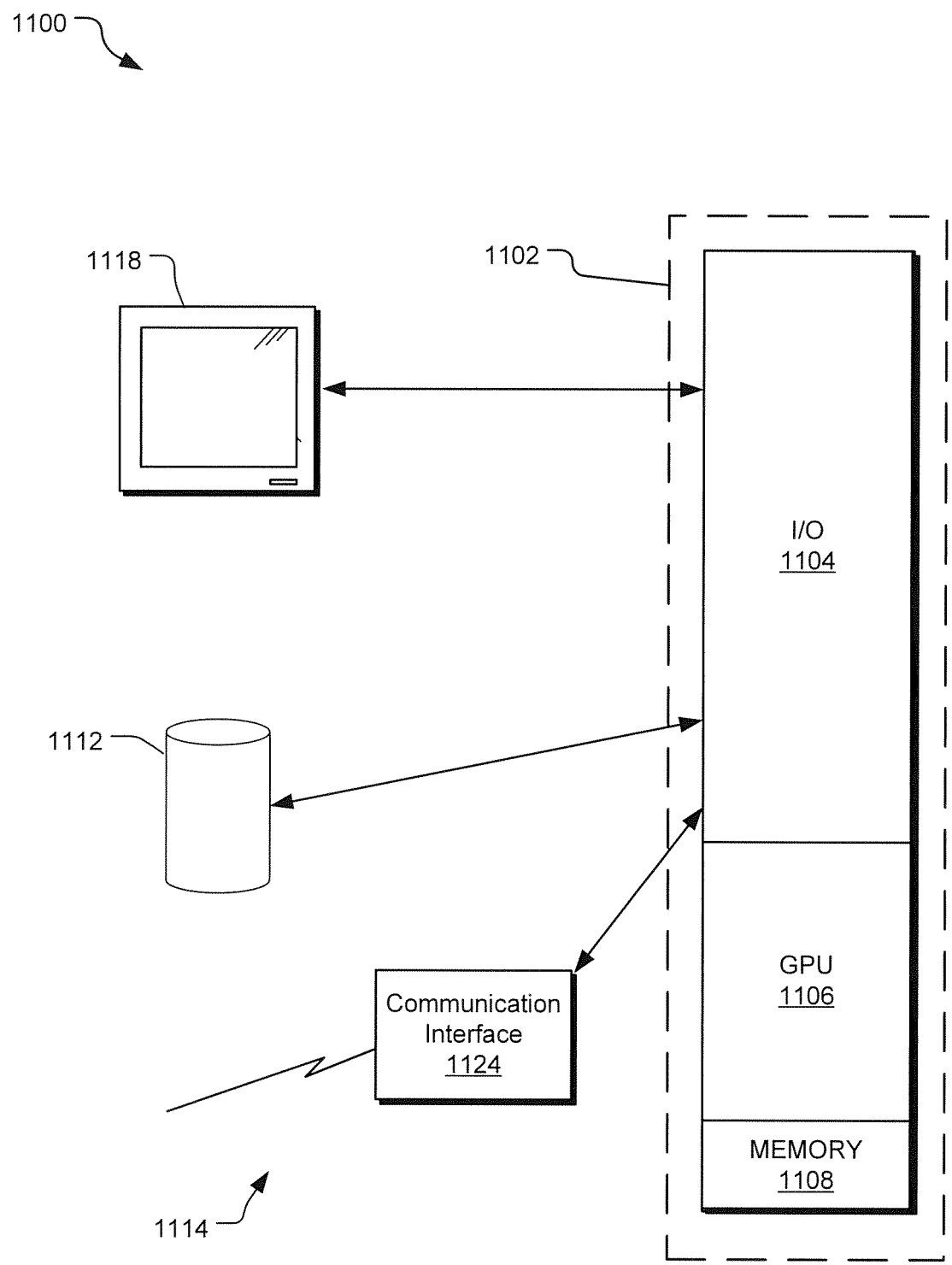
FIG. 11 illustrates a block diagram of an example computer system suitable for implementing one or more disclosed methods in the disclosed technology.

Referring to FIG. 11, a block diagram of an example computer system 1100 suitable for implementing one or more disclosed methods in the disclosed technology is shown. The computer system 1100 is capable of executing a computer program product embodied in a tangible computer-readable storage medium to execute a computer process for modeling progression of healthcare expenses.

The computer system 1100 may include a variety of tangible computer-readable storage media and intangible computer-readable communication signals. Tangible computer-readable storage can be embodied by any available media including both volatile and nonvolatile storage media, removable and non-removable storage media. Tangible computer-readable storage media excludes intangible and transitory communications signals and includes volatile and nonvolatile, removable and non-removable storage media implemented in any method or technology for storage of information such as computer readable instructions, data structures, program modules or other data. Tangible computer-readable storage media includes, but is not limited to, RAM, ROM, EEPROM, flash memory or other memory technology, CDROM, digital versatile disks (DVD) or other optical disk storage, magnetic cassettes, magnetic tape, magnetic disk storage or other magnetic storage devices, or any other tangible medium which can be used to store the desired information and which can accessed by the speech recognition device 400. In contrast to tangible computer-readable storage media, intangible computer-readable communication signals may embody computer readable instructions, data structures, program modules or other data resident in a modulated data signal, such as a carrier wave or other signal transport mechanism. The term "modulated data signal" means a signal that has one or more of its characteristics set or changed in such a manner as to encode information in the signal. By way of example, and not limitation, intangible communication signals include wired media such as a wired network or direct-wired connection, and wireless media such as acoustic, RF, infrared and other wireless media.

Data and program files may be input to the computer system 1100, which reads the files and executes the programs therein using one or more processors in a central computing device. Some of the elements of a computer system 1100 are shown in FIG. 11 wherein a processor 1102 is shown having an input/output (I/O) section 1104, a Central Processing Unit (CPU) or Graphics Processing Unit (GPU) 1106, and a memory section 1108. There may be one or more processors 1102, such that the processor 1102 of the computing system 1100 comprises a single CPU/GPU 1106, or a plurality of processing units. The processors may be single core or multi-core processors and usually require several GPU cores working in parallel. The computing system 1100 may be a conventional computer, a distributed computer, a central computing device (as described in FIG. 2) or any other type of computer. The described technology is optionally implemented in software loaded in memory 1108, a disc storage unit 1112, and/or communicated via a wired or wireless network link 1114 on a carrier signal (e.g., Ethernet, 3G wireless, 5G wireless, LTE (Long Term Evolution)) thereby transforming the computing system 1100 in FIG. 11 to a special purpose machine for implementing the described operations.

The I/O section 1104 may be connected to one or more user interface devices (e.g., a keyboard, a touch-screen display unit 1118, etc.) or a disc storage unit 1112 for user in out. Computer program products containing mechanisms to effectuate the systems and methods in accordance with the described technology may reside in the memory section 1104 or on the storage unit 1112 of such a system 1100.

A communication interface 1124 is capable of connecting the computer system 1100 to an enterprise network via the network link 1114, through which the computer system can receive instructions and data embodied in a carrier wave. When used in a local area networking (LAN) environment, the computing system 1100 is connected (by wired connection or wirelessly) to a local network through the communication interface 1124, which is one type of communications device. When used in a wide-area-networking (WAN) environment, the computing system 1100 may includes a modem, a network adapter, or any other type of communications device for establishing communications over the wide area network. When used across different WAN's, or over the internet, the computing system 1100 may provides a stateless interface (REST), which enables a client (e.g., a mobile device or any other computer) with little to no knowledge of the computing system 1100 to establish communications. In a networked environment, program modules depicted relative to the computing system 1100 or portions thereof, may be stored in a remote memory storage device. It is appreciated that the network connections shown are examples of communications devices for and other means of establishing a communications link between the computers may be used.

In an example implementation, a user interface software module and other modules (e.g., the event data module 220, the static database module 218, the dynamic database module 216, and the computer modeling module 214 in FIG. 2) may be embodied by instructions (e.g., instructions for operations 500 in FIG. 5) stored in memory 1108 and/or the storage unit 1112 and executed by the processor 1102. Further, local computing systems, remote data sources and/ or services, and other associated logic represent firmware, hardware, and/or software, which may be configured to assist the disclosed methods. A system may be implemented using a general purpose computer and specialized software (such as a server executing service software), a special purpose computing system and specialized software (such as a mobile device or network appliance executing service software), or other computing configurations.

The implementations of the technology described herein can be implemented as logical steps in one or more computer systems. The logical operations of the present invention are implemented (1) as a sequence of processor-implemented steps executing in one or more computer systems and (2) as interconnected machine or circuit modules within one or more computer systems. The implementation is a matter of choice, dependent on the performance requirements of the computer system implementing the invention. Accordingly, the logical operations making up the embodiments of the invention described herein are referred to variously as operations, steps, objects or modules. Furthermore, it should be understood that logical operations may be performed in any order, adding and omitting as desired, unless explicitly claimed otherwise or a specific order is inherently necessitated by the claim language.

The above specification, examples, and data provide a complete description of the structure and use of exemplary implementations of the disclosed technology. Since many implementations can be made without departing from the spirit and scope of the invention, the invention resides in the claims hereinafter appended.

What is claimed:

1. A system for modeling progression of healthcare expenses, comprising:
a central computing device configured to:
communicate with healthcare event data generation sources to obtain healthcare event data including a plurality of healthcare events resulting in out-of-pocket expenditures per a given healthcare plan, the central computing device further configured to store the healthcare event data in hierarchical layered graphs in a static database module, each higher level of the hierarchical layered graphs collapsing at least one sub-graph structure of a lower level graph into a single node, the hierarchical graphs including:
at least one graph including interconnected nodes representing health care plan factors for different individuals; and
a highest level graph representing a Bayesian belief network defined by nodes interconnected by edges indicating causal relationships between the nodes of one or more lower level graphs of the hierarchical layered graphs, each of the nodes further representing at least one health care event and an associated cost;
a computer module stored in memory and configured to:
use machine learning techniques to traverse the hierarchical layered graphs to create higher level representations of the healthcare event data as a synthesized knowledge graph, the synthesized knowledge graph associating ages and health conditions with event nodes representing different clusters of events, each of the event nodes being stored in association with a probability distribution for at least one of an age and a health condition;
use the synthesized knowledge graph to simulate multiple paths for an individual based on user inputs including health care plan factors for the individual, each one of the paths representing a predicted series of future healthcare expenditures over an estimated lifespan from a current year;
aggregate and coalesce the multiple paths into fewer paths by stitching together paths corresponding to classes of individuals of similar age; and
use the aggregated and coalesced paths of the synthesized knowledge graph and the probability distributions associated with the event nodes along each of the paths to determine a most likely set of the future healthcare expenditures for the individual.

2. The system of claim 1, wherein the central computing device comprises a big data engine that receives user data and forecasts lifetime expenditures.

3. The system of claim 1, wherein the out-of-pocket expenditures are events caused by at least one of a chronic condition and an infectious disease.

4. The system of claim 1, wherein the system creates a probabilistic causal model relating each path with individual context determined by a plurality of the nodes the individual is connected to.

5. The system of claim 4, wherein the causal condition is a chronic condition.

6. The system of claim 1, wherein the static database module comprises information about individuals in a predetermined population, including at least one of age, race, sex, location, healthcare plan type, prevalence of diseases, and expenditure causing events.

7. The system of claim 1, wherein the static database module includes information about cost variabilities in treatment based on personal factors.

8. The system of claim 1, wherein the healthcare event data comprises at least one of susceptible individuals, individuals given therapeutic treatment, individuals treated prophylactically, individuals given no treatment, cumulative number of total individuals with the disease, cumulative number of action taken at early stage, cumulative number of treated individuals with no action taken at early stage, cumulative number of hospitalized individuals with no action taken, cumulative number of hospitalized individuals with action taken at an early stage, days of hospital stay per individual for individuals with no action taken at early stage, and days of hospital stay per individual for individuals with some action taken at early stage.

9. A method of modeling progression of healthcare expenses comprising:
  accessing a plurality of healthcare event data from healthcare event data generation sources;
  storing the healthcare event data in hierarchical layered graphs in memory within a static database module in a central computing device, each higher level of the hierarchical layered graphs collapsing at least one sub-graph structure of a lower level graph into a single node, the hierarchical graphs including:
  at least one graph including interconnected nodes representing health care plan factors for different individuals; and
  a highest level graph of the hierarchical layered graphs representing a Bayesian belief network defined by nodes interconnected by edges indicating inferred causal relationships between the nodes of one or more lower level graphs of the hierarchical layered graphs, each of the nodes further representing at least one health care event and an associated cost;
  using machine learning techniques to traverse the hierarchical layered graphs to create higher level representations of the healthcare event data as a synthesized knowledge graph, the synthesized knowledge graph associating patient ages and health conditions with event nodes representing different clusters of events, each of the event nodes being stored in association with a probability distribution for at least one of an age and a health condition;
  using the synthesized knowledge graph to simulate multiple paths for an individual based on user inputs including health care plan factors for the individual, each one of the paths representing a predicted series of future healthcare expenditures over an estimated lifespan from a current year;
  aggregating and coalescing the multiple paths into fewer paths by stitching together paths corresponding to classes of individuals of similar age; and
  using the aggregated and coalesced paths of the synthesized knowledge graph and the probability distributions associated with the event nodes along each of the paths to determine a most likely set of the future healthcare expenditures for the individual.

10. The method of claim 9, further comprising aggregating temporal event data at an individual level in layered graphs in the static database module.

11. The method of claim 9, further comprising representing the static database as a graph of vertices and edges, and wherein the static database module uses machine learning techniques to identify similar paths.

12. The method of claim 9, further comprising periodically updating the static database module to revise beliefs in the Bayesian Belief network.

13. The method of claim 9, further comprising calculating multiple thousand paths for a given individual using data from the Bayesian Belief network with the computer modeling module.

14. The method of claim 9, further comprising periodically updating the healthcare event data in the static database module through historical claim and plan profile data to update the Bayesian belief network.

15. The method of claim 9, wherein aggregating and coalescing the multiple paths into fewer paths further comprises: stitching together individual trajectories based on correlations between an individual's current age and surviving age.

16. One or more tangible computer-readable storage media encoding computer executable instructions for executing on a computer system a computer process, the computer process comprising:
  accessing a plurality of healthcare event data from healthcare event data generation sources;
  storing the healthcare event data in hierarchical layered graphs in memory within a static database module in a central computing device, each higher level of the hierarchical layered graphs collapsing at least one sub-graph structure of a lower level graph into a single node, the hierarchical layered graphs including:
  at least one graph including interconnected nodes representing health care plan factors for different individuals; and
  a highest level graph representing a Bayesian belief network defined by nodes interconnected by edges indicating inferred causal relationships between the nodes of, one or more lower level graphs of the hierarchical layered graphs, each of the nodes further representing at least one health care event and an associated cost;
  using machine learning techniques to traverse the hierarchical layered graphs to create higher level representations of the healthcare event data as a synthesized knowledge graph, the synthesized knowledge graph associating patient ages and health conditions with event nodes representing different clusters of events, each of the event nodes being stored in association with a probability distribution for at least one of an age and a health condition;
  using the synthesized knowledge graph to simulate multiple paths for an individual based on user inputs including health care plan factors for the individual, each one of the paths representing a predicted series of future healthcare expenditures over an estimated lifespan from a current year;
  aggregating and coalescing the multiple paths into fewer paths by stitching together paths corresponding to classes of individuals of similar age; and
  using the aggregated and coalesced paths of the synthesized knowledge graph and the probability distributions associated with the event nodes along each of the paths to determine a most likely set of the future healthcare expenditures for the individual.

17. The system of claim 1, wherein the computer module is configured to utilize the hierarchical layered graphs to simulate multiple paths for an individual based on user inputs including a geographical location of the individual.

* * * * *